US007385086B2

(12) United States Patent
Townsend et al.

(10) Patent No.: US 7,385,086 B2
(45) Date of Patent: Jun. 10, 2008

(54) ANTIMICROBIAL COMPOUNDS

(75) Inventors: Craig A. Townsend, Baltimore, MD (US); James D. Dick, Upperco, MD (US); Gary R. Pasternack, Baltimore, MD (US); Francis P. Kuhajda, Lutherville, MD (US); Nicole M. Parrish, Ellicott City, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 10/764,451

(22) Filed: Jan. 27, 2004

(65) Prior Publication Data

US 2004/0186176 A1 Sep. 23, 2004

Related U.S. Application Data

(62) Division of application No. 09/486,550, filed as application No. PCT/US98/17830 on Aug. 28, 1998, now Pat. No. 6,713,654.

(60) Provisional application No. 60/056,272, filed on Aug. 29, 1997.

(51) Int. Cl.
  *C07C 317/00* (2006.01)
  *C07C 317/02* (2006.01)
  *C07C 317/04* (2006.01)
  *C07C 317/06* (2006.01)
  *C07C 317/08* (2006.01)

(52) U.S. Cl. .............................. 568/27; 568/28; 568/31; 514/550; 514/618

(58) Field of Classification Search .................. 568/27, 568/28, 31; 514/546, 601
See application file for complete search history.

(56) References Cited

U.S. PATENT DOCUMENTS

| | | | |
|---|---|---|---|
| 4,123,254 | A | 10/1978 | Iwasaki et al. |
| 5,530,113 | A | 6/1996 | Christ et al. |
| 5,614,551 | A | 3/1997 | Dick et al. |
| 5,759,837 | A | 6/1998 | Kuhajda et al. |
| 5,981,575 | A | 11/1999 | Kuhajda et al. |

FOREIGN PATENT DOCUMENTS

| | | |
|---|---|---|
| DE | 2630947 | 2/1977 |
| DE | 2729685 | 1/1978 |
| DE | 2812542 | 10/1979 |
| GB | 1557225 | 12/1979 |
| WO | 9519706 | 7/1995 |
| WO | WO 95/19706 | 7/1995 |

OTHER PUBLICATIONS

Jones, P. B.; Parrish, N. M.; Houston, T. A.; Stapon, A.; Bansal, N. P.; Dick J. D.; Townsend, C. A. "A New Class of Antituberculosis Agents" J. Med. Chem. 2000, 43, 3304-3314.*

Cassady, D. R.; Ainsworth, C.; Easton, N. R.; Livezey, M.; Sigal, M. V.; Heyningen, E. V. "Sulfonylureas and related compounds" J. Org. Chem. 1958, 23, 923-6.*

Janczewski, M.; Janowski, W. "Synthesis of racemic p-methylbenzylsulfinylaceitc acid and its reslolution into optical antipodes." Ann. Univ. Mariae Curie-Sklodowska, Sect. AA 1978, 33, 139-55.*

Narr, B.; Nickl, J.; Roch, J.; Mueller, E.; Eisele, B.; Leitold, M. "Sulfur-containing fluorenyl and phenanthryl derivatives" DE 2812542, 1979.*

Solomons G. T. W. Organic Chemistry (Fifth Edition). New York: John Wiley & Sons, Inc., p. 65.*

Guerardel et al., "Structural Study of Lipomannan and Pioarabinomannan from Mycobacterium chelonae" J. Biol. Chem. 2002, 277(34), 30635-30648.*

Kurashima, A. "The short-term effects of multidrug chemotherapy for pulmonary Mycobacterium avium-intracellulare complex (MAC) infection" Kekkaku, 1998, 73(5), abstract only.*

Parrish et al. "In vitro Activity of a Novel Antimycobacterial Compound, N-Octanesulfonylacetamide, and Its Effects on Lipid and Mycolic Acid Synthesis" Antimicrobial Agents and Chemotherapy 2001, 45(4), 1143-1150.*

Rieder H. L. (2002) Interventions for tuberculosis control and elimination, International Union Against Tuberculosis and Lung Disease, Paris, pp. 45 and 46.*

Nuremberger et al. "Pharmacokinetic andPharmacodynamic Issuesin the Treatment of Mycobacterial Infections" Eur. J. Clin. Microbiol. Infect. Dis. 2004, 23, 243-255.*

Burman, W. J. "The value of in vitro drug activity and pharmacokinetics in predicting the effectiveness of antimycobacterial therapy: a critical review" Am. J. Med. Sci. 1997, 313(6), 355-363.*

Fernanda et al., "Construction of a promoter trap to identify virulence genes in mycobacterium tuberculosis", Molecular Mechanisms in Tuberculosis Keystone Symposium, Feb. 19-25, 1995, abstract.*

(Continued)

*Primary Examiner*—Jon D. Epperson
(74) *Attorney, Agent, or Firm*—Hunton & Williams LLP

(57) ABSTRACT

This invention provides compounds and methods for treating, with said compound, a mycobacterial infection by administering to an animal a pharmaceutical composition containing a compound having the formula $R-SO_n-Z-CO-Y$, where R is an alkyl groups having 6-20 carbon atoms, unsaturated hydrocarbon groups having 6-20 carbon atoms, or alkyl groups having 6-20 carbon atoms interrupted by at least one aromatic ring; Z is $-CH_2-$, $-CH_2CH_2-$, $-NH-NH-$, $-O-$, $-NH-$, $-O-NH-$, $-CH_2-NH-$, $-CH_2-O-$, $-NH-O-$, $-NH-CH_2-$, $-O-CH_2-$, and $-CH=CH-$; Y is $-NH_2$, $-O-CH_2-C_6H_5$, $-CO-CO-O-CH_3$, and $-O-CH_3$; and n is 1 or 2. It has been discovered that these compounds treat microbially-based infections caused by corynebacteria, nocardiae, rhodococcus, and mycobacteria. These compounds may be used to treat mycobacterial cells, such as *Mycobacteria tuberculosis*, drug resistant *M. tuberculosis*, *M. avium intracellulare*, *M. leprae*, *M. paratuberculosis*, and pathogenic *Mycobacteria* sp.

11 Claims, 4 Drawing Sheets

OTHER PUBLICATIONS

Marcel et al. "1H- and 13C-NMR studies on sulfinyl and sulfonyl derivatives of positional isomers of methyl thialaurate", Chemistry and Physics of Lipids, 1992, 61, pp. 139-147.*

2-(dodecanesulfonyl) acetamine, Toxic Substances Control Act Inventory List (1998).

Baldock C., Rafferty J.B., Sedenikova S.E., Baker P.J., Stuitje A.R., Slabas A.R., Hawkes T.R., Rice D.W. "A mechanism of drug action revealed by structural studies of enoyl reductase," Science, 274:2107-2110, 1996.

Banerjee, A., E. Dubnau, A. Quemard, V. Balasubramanian, K.S. Um, T. Wilson, D. Collins, G. deLisle, W.R. Jacobs, Jr., "InhA, a gene encoding a target for isoniazid and ethionamide in Mycobacterium tuberculosis," Science, 263:227-230, 1994.

Bloch, K., "Control mechanisms for fatty acid synthesis in Mycobacterium smegmatis," Adv. Enzymol. 45:1-84, 1977.

Brennan, P.J., and Nikaido, H., "The envelope of mycobacteria," Ann. Rev. Biochem., 64:29-63, 1995.

Cassady D. et al., "Sulfonylureas and related compounds," J. Org. Chem. 23:923-6, 1958.

Dessen A., A. Quemard, J.S. Blanchard, W.R. Jacobs, and J.C. Saccettini, "Crystal structure and function of the isoniazid target of Mycobacterium tuberculosis," Science, 267: 1638-1641, 1995.

Georges C. et al., "Chiral sulphur-containing molecules in Langmuir-Blodgett films," J. Chem. Soc. Faraday Trans. I, 84(5):1531-1542, 1988.

Hardy F. et al., "Vanadium pentoxide-catalyzed oxidation of thio-compounds with hydrogen peroxide," J. Chem. Sec., 17:2334-2336, 1969.

Janczewski M. et al., "Synthesis if racemic p-methylbenzylsulfinylacetic acid and its resolution into optical antipodes," Ann. Univ. Mariae Curie-Sklodowska, Sect. AA, 33:139-55, 1978.

Lie M. et al., "$^1$H- and $^{13}$C-NMR studies on sulfinyl and sulfonyl derivatives of positional isomers of methyl thialaurate," Chemistry and Physics of Lipids, 61:139-147, 1992.

Mdluli, K., D.R. Sherman, M.J. Hickey, B.N. Kreiswirth, S. Monis, C.K. Stover, and C.E. Bay, III, "Biochemical and genetic data suggest that InhA is not the primary target for activated isoniazid in Mycobacterium tuberculosis," J. Infect. Dis., 174:1085-1090, 1996.

Mikolajczyk M. et al., "NMR and structural assignments in α,β-unsaturated sulphoxides using addictive increments method," Tetrahedron, 32:969-973 (1976).

Quemard A. et al., "Binding of catalase-peroxidase-activated isoniazid to wild-type and mutant Mycobacterium tuberculosis enoyl-ACP reductases," J. Am. Chem. Soc., 118:1561-1562, 1996.

Quemard A. et al., "Enzymatic characterization of the target for isoniazid in Mycobacterium tuberculosis," Biochemistry, 34(26):8235-8241, 1995.

Solomons G.T., Organic Chemistry (Fifth Edition) (New York: John Wiley & Sons, Inc.), p. 65.

Takayama, K., Wang, L., and David, H.L., "Effect of isoniazid on the in vivo mycolic acid synthesis, cell growth, and viability of Mycobacterium tuberculosis," Antimicrob. Agents Chemother., 2:29-35, 1972.

Takayama, K., Schnoes, H.K., Armstrong, E.I., and Booyle, R.W., "Site of inhibitory action of isoniazid in the synthesis of mycolic acids in Mycobacterium tuberculosis," J Lipid Res., 16:308-317, 1975.

Young, D.B., and Duncan, K., "Prospects for new interventions in the treatment and prevention of mycobacterial disease," Ann Rev. Microbiol., 49:641-673, 1995.

Hardy, Frederick E., et al. "Vanadium pentoxide-catalyzed oxidation of thio-compounds with hydrogen peroxide", J. Chem. Soc., 1969, 17, pp. 2334-2336. (Abstract).

2-(dodecanesulfonyl) acetamide, Toxic Substances Control Act Inventory List (1998).

Lie, Marcel S.F., Ken Jie and Oladapo Bakare. "$^1$H- and $^{13}$C-NMR studies on sulfinyl and sulfonyl derivatives of positional isomers of methyl thialaurate", Chemistry and Physics of Lipids, 1992, 61, pp. 139-147.

Georges, Christian et al. "Chiral Sulphur-containing Molecules in Langmuir-Blodgett Films", J. Chem. Soc. Faraday Trans. I, 84 (5), pp. 1531-1542.

Mikolajczyk, M. et al. "NMR and Structural Assignments in α,β-Unsaturated Sulphoxides Using Addictive Increments Method", Tetrahedron, 1976, vol. 32, pp. 969-973.

Quemard, Annaik et al. "Enzymatic Characterization of the Target for Isoniazid in Mycobacterium tuberculosis", Biochemistry, 1995, vol. 34, No. 26, pp. 8235-8241.

Baldock, Clair et al. "A Mechanism of Drug Action Revealed by Structural Studies of Enoyl Reductase", Science, vol. 274, Dec. 20, 1996, pp. 2107-2110.

Quemard, Annaik et al. "Binding of Catalase-Peroxidase-Activated Isoniazid to Wild-Type and Mutant Mycobacterium tuberculosis Enoyl-ACP Reductases", J. Am. Chem. Soc., 1996, 118, pp. 1561-1562.

* cited by examiner

ANTIMICROBIAL COMPOUNDS

CROSS-RELATED AND PRIORITY APPLICATIONS

This application is a divisional application of U.S. application Ser. No. 09/486,550, filed Aug. 28, 2000, now U.S. Pat. No. 6,713,654, which is the National Phase under 35 U.S.C. § 371 of PCT/US98/17830, filed Aug. 28, 1998, which claims benefit of priority of U.S. application Ser. No. 60/056,272, filed Aug. 29, 1997. These priority documents are hereby incorporated by reference in their entirety.

BACKGROUND OF THE INVENTION

1. Field of the Invention

This invention relates to the synthesis and in vivo application of compounds which have antibiotic activity against microbes that synthesize mycolic acid, including *Mycobacterium* sp., particularly drug resistant *Mycobacterium* strains, and to the use of these compounds to treat any susceptible pathogenic microorganism or parasite.

2. Review of Related Art

The emergence of multiply drug resistant (MDR) strains of *Mycobacterium tuberculosis* and other atypical mycobacteria which infect immunocompromised patients (e.g., AIDS patients) highlights the need for continued antibiotic development.

*Mycobacterium* sp. synthesize a multitude of complex lipids and glycolipids unique to this genus, making these biochemical pathways attractive targets for drug therapy (Bloch, K., "Control mechanisms for fatty acid synthesis in Mycobacterium smegmatis," *Adv. Enzymol.* 45:1-84, 1977; Brennan, P. J., and Nikaido, H., "The envelope of mycobacteria," *Ann. Rev. Biochem.* 64:29-63, 1995). The β-ketoacyl synthase (KS) of particulate Type II fatty acid synthases or the corresponding domain of the polyfunctional Type I fatty acid synthases catalyzes the critical two-carbon homologation during buildup of the growing fatty acid chain. This process typically gives acids of length $C_{16}$ to $C_{18}$. In chain elongation of normal fatty acids, carried out for example by mycobacteria, CoA and/or acyl-carrier protein (ACP) thioesters of these acids are further reacted with malonyl-CoA to greatly extend their length to 60-90 carbons. These high molecular weight acids are known collectively as mycolic acids.

Mycolic acids are a group of complex, long, branched chain fatty acids that are vital for the growth and survival of mycobacteria. Mycolic acids comprise the single largest component of the mycobacterial cell envelope. Little is known about the nature of the biosynthetic enzymes involved, but evidence suggests some similarity to conventional fatty acid synthases (Bloch, 1977; Brennan, et al., 1995). These unusually long lipid molecules form a waxy coat of limited permeability.

The presence in mycobacteria of particular modified fatty acids having complex and well-organized structures presents a potentially attractive target for drug design (Young, D. B., and Duncan, K., "Prospects for new interventions in the treatment and prevention of mycobacterial disease," *Ann Rev. Microbiol.* 49:641-673, 1995). It has been suggested that isoniazid inhibits mycolic acid synthesis as its potential mechanism of action (Takayama, K., Wang, L., and David, H. L., "Effect of isoniazid on the in vivo mycolic acid synthesis, cell growth, and viability of *Mycobacterium tuberculosis*," *Antimicrob. Agents Chemother.*, 2:29-35, 1972; Takayama, K., Schnoes, H. K., Armstrong, E. I., and Booyle, R. W., "Site of inhibitory action of isoniazid in the synthesis of mycolic acids in *Mycobacterium tuberculosis*," *J. Lipid Res.*, 16:308-317, 1975; Quemard A., Dessen A., Sugantino M., Jacobs W. R., Sacchettini J. C., Blanchard J. S. "Binding of catalase peroxide-activated isoniazid to wild-type and mutant *Mycobacterium tuberculosis* enoyl-ACP reductases," *J. Am. Chem. Soc.*, 118:1561-1562, 1996; Baldock C., Rafferty J. B., Sedenikova S. E., Baker P. J., Stuitje A. R, Slabas A. R., Hawkes T. R., Rice D. W. "A mechanism of drug action revealed by structural studies of enoyl reductase," *Science*, 274:2107-2110, 1996; Quemard A., Sacchettini J. C., Dessen A., Vilcheze C., Bittman R., Jacobs W. R., Blanchard J. S., "Enzymatic characterization of the target for isoniazid in *Mycobacterium tuberculosis, Biochemistry*, 34:8235-8241, 1993; Msluli, K., D. R. Sherman, M. J. Hickey, B. N. Kreiswirth, S. Morris, C. K. Stover, and C. E. Barry, III, "Biochemical and genetic data suggest that InhA is not the primary target for activated isoniazid in *Mycobacterium tuberculosis*," *J. Infect. Dis.*, 174:1085-1090, 1996; Dessen A., A. Quemard, J. S. Blanchard, W. R. Jacobs, and J. C. Saccettini, "Crystal structure and function of the isoniazid target of *Mycobacterium tuberculosis*," *Science*, 267:1638-1641, 1995; Banerjee, A., E. Dubnau, A. Quemard, V. Balasubramanian, K. S. Um, T. Wilson, D. Collins, G. deLisle, W. R. Jacobs, Jr., "InhA, a gene encoding a target for isoniazid and ethionamide in *Mycobacterium tuberculosis*." *Science*, 263:227-230, 1994). This finding might be expected to stimulate a search for novel compounds that act upon the lipid synthetic pathways of mycobacteria as a fresh approach for antibiotic development. Surprisingly, however, lipid biosynthesis has not been exploited for drug development in these organisms. No drugs which specifically inhibit mycobacterial lipid synthesis have been developed other than isoniazid, and there remains a need for new drugs to treat the growing problem of multi-drug resistant mycobacteria.

SUMMARY OF THE INVENTION

This invention is directed to novel compounds having antimicrobial activity, particularly antimicrobial effectiveness against multi-drug resistant mycobacteria.

This invention is also directed to a method for treating mycobacterial infection by drug resistant strains through use of independent therapeutic targets.

These and other objects of the invention are achieved by one or more of the following embodiments. In one embodiment, this invention provides a compound having the formula: R—SO$_n$-Z-CO—Y, where R is preferably an alkyl group having 6-20 carbons; Z is preferably a radical selected from —CH$_2$—, —O—, and —NH—, two of these radicals coupled together or —CH$_2$=CH$_2$—; Y is preferably —NH$_2$, —O—CH—C$_2$H$_6$, —CO—CO—O—CH$_3$, or —O—CH$_3$; and n is 1 or 2. In particularly preferred embodiments. R is a branched alkyl group, or R is a linear alkyl group interrupted by an aromatic ring.

In another embodiment, this invention provides a method of inhibiting growth of a microbial cell which synthesizes α-substituted, β-hydroxy fatty acids. The method comprising treating the cell with a compound having the formula: R—SO$_n$-Z-CO—Y, as described above. In particular; cells inhibited by the compound of this invention are cells which synthesize α-substituted, β-hydroxy fatty acids selected from the group consisting of corynemycolic acid, nocardic acid, and mycolic acid. Preferably, the method is used to inhibit growth of microbial cells selected from the group consisting of corynebacteria, nocardiae, rhodococcus, and mycobacteria. More preferably, the method is used to inhibit growth of mycobacterial cells, such as *Mycobacterium tuberculosis*, drug-resistant *M. tuberculosis*, *M. avium intracellulare*, *M. leprae*, or *M. paratuberculosis*.

In yet another embodiment, this invention provides a method for treating a mycobacterial infection by administering to an animal a pharmaceutical composition containing a compound having the formula: R—SO$_n$-Z-CO—Y, as described above.

The present inventors have synthesized and tested a number of sulfones and sulfoxides having structures based upon the reaction intermediates of the β-ketoacyl synthase reaction of fatty acid synthase. A .number of these compounds have demonstrated in vitro activity against virulent *M. tuberculosis* (see Table 1). The desireable characteristics found among the compounds tested included: potency, in vivo activity, reproducibility of MIC data, ease of synthesis, and chemical stability. Use of the compounds of this invention in drug therapy against multiply drug resistant tuberculosis will provide a means to treat both patients presently suffering from active disease, and the millions of potential patients who harbor quiescent disease which may become active as a result of immunosuppression or other systemic disease.

DETAILED DESCRIPTION OF THE EMBODIMENTS

The compounds synthesized according to this invention are based on theoretical transition-state intermediates of the β-ketoacyl synthase reaction of fatty acid synthase (E.C. 2.3.1.85). The β-ketoacyl synthase reaction is common to fatty acid synthesis in prokaryotes and eukaryotes, including *Mycobacteria*. The family of compounds shown in Table 1 was found to be cytotoxic against a variety of mycobacteria, including drug resistant strains. Instead of inhibiting Type I/Type II fatty acid synthesis in mycobacteria, however, Compound HIII-50 (III-50) inhibits the synthesis of mycolic acids, specialized fatty acids found particularly in *Mycobacteria* sp. One of the key steps in mycolic acid synthesis is fatty acid elongation, which employs carbon-carbon condensation similar to the β-ketoacyl synthase reaction in de novo fatty acid synthesis. It is believed that these compounds act at this fatty acid elongation step critical to mycolic acid synthesis.

Figure 1:
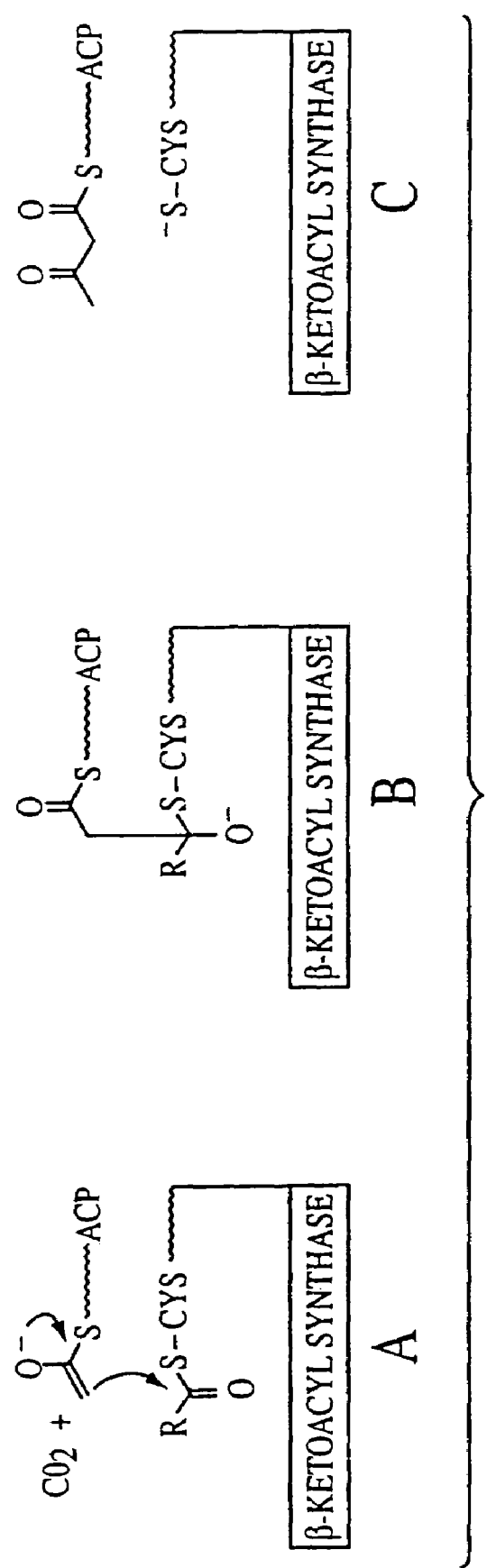
FIG. 1 shows a schematic representation of the β-ketoacyl synthase reaction.

The transition states for all of the two-carbon elongation reactions are presumed, on existing biochemical evidence and mechanistic grounds, to be quite similar (see FIG. 1) and involve acylanion formation by decarboxylation of malonyl-CoA/ACP to provide a nucleophile (FIG. 1, step A) to react with the thioester-bound acyl chain to generate tetrahedral intermediate (FIG. 1, step B). This transient intermediate is anticipated to collapse (FIG. 1, step C) to extend the growing acyl unit (RCO—) by two carbons. Further steps then reduce the β-keto group of the ACP/CoA derivative and finally return it to step A to begin the chain extension cycle again.

Low molecular weight organic compounds which are potential mimics of the tetrahedral intermediate (see stepB) may be expected to be inhibitors of this biochemical process, and such compounds are represented by Formula I.

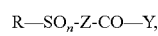

R—SO$_n$-Z-CO—Y, Formula I wherein R is hydrocarbon, such as an alkyl group;

n is 1 or 2;

Z is a hydrocarbon linking moiety that may contain a heteroatom; and

Y is a hydrocarbon end group moiety that may contain one or more heteroatoms.

In preferred compounds according to Formula I, R may be an n-alkyl group having 6-20 carbons, preferably 8, 10 or 12 carbons, and may be saturated or unsaturated, branched or unbranched, or the alkyl chain may be interrupted by a aromatic ring to give ortho-, meta-, or para-disubstitution. Z is preferably —CH$_2$—, —CH$_2$—CH$_2$—, cis or trans —CH=CH—, —NH—CH$_2$—, —CH$_2$—NH—, —O—CH$_2$—, or —CH$_2$—O—, and Y is preferably —NH$_2$, —O—CH$_2$—C$_6$H$_5$, —CO—O—CH$_3$ —CO—CO—O—CH$_3$ or —O—CH$_3$. Between R and Z is a sulfur atom in the form of a sulfoxide or sulfone. The sulfone III-50 and close structural analogues with shorter and longer saturated and unsaturated alkyl side chains, as well as alternative mimics of the tetrahedral intermediate of step B are exemplified but not exclusively represented by the structures shown in Table 1.

The compounds of Formula I may be synthesized by a variety of routes including alkylation of a mercaptoester to produce a thioether (see, e.g., R. L. Smith et al., *J. Med. Chem.*, 1977, 20:540-547), followed by oxidation to afford a sulfoxide or sulfone and conversion of the ester to an amide with ammonia or a substituted amine. A suitable synthetic scheme is shown in Scheme 1 and exemplified in Example 1.

Scheme 1

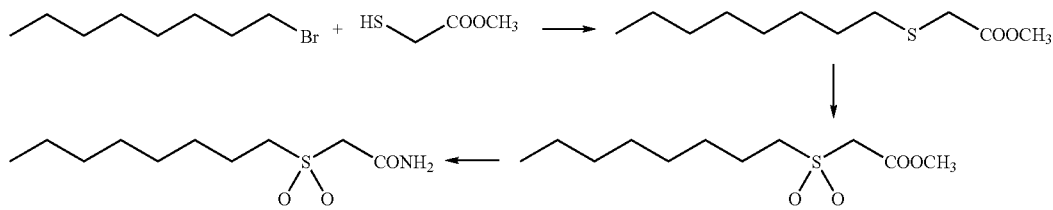

Alternatively, a sulfonate salt, for example the sodium salt, may be reacted with a haloester to give a thioether (i.e. $R-SO_2-Na^+ + X-(CH_2)_n-COOR' \rightarrow R-SO_2-(CH_2)_n-COOR'$; see, e.g., E. Gipstein, C. G. Willson and H. S. Sachdev, *J. Org Chem.,* 1980, 45:1486-1489), which can be oxidized and ammonolyzed to the corresponding amide as above. Typically, X=Cl, Br or I. A second alternative would be reaction of a haloamide ($X-(CH_2)_n-CONH_2$) with either a sulfonate salt, as above, or with a thiolate anion followed by oxidation to similarly yield the sulfonyl amide or the sulfoxide amide (see, e.g., S. Huenig and O. Boes, *Liebigs Annalen der Chemie,* 1953, 579:23-26). It will be apparent to the skilled worker that the sense of these reactions can be reversed so that a halohydrocarbon may be reacted with a mercaptoamide or the salt of a sulfenylamide or sulfenylester to obtain the same products. A third alternative would be reaction of a thiol (R—SH) with propiolate ester or amide to form a sulfanyl-acrylic ester or amide followed by oxidation to the sulfoxide or sulfone. Finally, a halo- or mercaptonitriles can be reacted by the above schemes to give thioethers or sulfonylnitriles, which can be hydrolyzed to the amides. Where other alternative synthetic routes to produce the compounds of Formula I occur to the skilled worker, the products of such synthesis are also within the contemplation of this invention.

The compounds according to Formula I may be used as antibiotics against microbes having in their cell walls α-substituted, β-hydroxy fatty acids, such as corynemycolic acids (e.g., C30), nocardic acids (e.g., C50) or mycolic acids (e.g., C90). Unless otherwise indicated, use of the term mycolic acids herein refers to any of these long chain α-substituted, β-hydroxy fatty acids. In particular, compounds according to Formula I exhibit antibiotic activity against corynebacteria, nocardiae, rhodococcus and *mycobacteria*. More particularly, these compounds are effective against *Mycobacterium tuberculosis*, drug-resistant *M. tuberculosis*, *M. avium intracellulare*, *M. leprae*, or *M. paratuberculosis*.

Preferred compounds according to Formula I will have substantial antibiotic activity against susceptible organisms (see, e.g., Table 1). Antibiotic effectiveness of compounds according to Formula I may be determined as described below or by use of assays described in U.S. Pat. No. 5,614,551, which is incorporated herein by reference. In particulr, U.S. Pat. No. 5,614,551 describes an in vitro therapeutic index based on comparison of the concentration which inhibits growth of normal fibroblasts to the minimal inhibitory concentration for a compound, and preferred compounds will have an in vitro therapeutic index of at least 2, more preferably at least 5, and most preferably at least 10.

Novel drug therapy, using compounds of this invention which are effective against multiply drug resistant tuberculosis, will aid in treating both patients presently suffering from active disease, and the millions of potential patients who harbor quiescent disease which may become active as a result of immunosuppression or other systemic disease. These drugs will also be useful against the, "atypical mycobacteria" such as *M. avium-intracellulare*, a common AIDS pathogen, and other species that are commonly drug resistant. Given the biochemical similarity between *M. tuberculosis* and *M. leprae*, these drugs may be expected to be useful in the treatment of leprosy (Hansen's disease). Potential use in livestock or other veterinary applications include treatment of infections by *Mycobacterium paratuberculosis*, also known as Johne's bacillus, an organism that produces a chronic enteritis in ruminants (e.g., cattle and sheep) which is invariably fatal, and *Rhodococcus*, another organism which produces mycolic acids as well as potentially fatal respiratory infections in horses and immunocompromised patients. Treatment of human patients infected with *M. paratuberculosis* is also within the contemplation of this invention.

Treatment according to this invention involves administering the compound of Formula I to the subject of treatment. Pharmaceutical compositions containing any of the compounds of this invention may be administered by parenteral (subcutaneously, intramuscularly, intravenously, intraperitoneally, intrapleurally, intravesicularly or intrathecally), topical, oral, rectal, or nasal or inhalation route, as necessitated by choice of drug, pharmaceutical carrier, and disease.

Therapeutic compounds according to this invention are preferably formulated in pharmaceutical compositions containing the compound and a pharmaceutically acceptable carrier. The Concentrations of the active agent in pharmaceutically acceptable carriers will depend on solubilities. The dose used in a particular formulation or application will be determined by the requirements of the particular type of disease and the constraints imposed by the characteristics and capacities of the carrier materials. The pharmaceutical composition may contain other components so long as the other components do not reduce the effectiveness of the compound according to this invention so much that the therapy is negated. Pharmaceutically acceptable carriers are well known, and one skilled in the pharmaceutical art can easily select carriers suitable for particular routes of administration (see, e.g., *Remington's Pharmaceutical Sciences*, Mack Publishing Co., Easton, Pa., 1985).

Dose and duration of therapy will depend on a variety of factors, including the therapeutic index of the drugs, disease type, patient age, patient weight, and tolerance of toxicity. Dose will generally be chosen to achieve serum concentrations from about 1 ng to about 100 µg/ml, typically 0.1 µg/ml to 10 µg/ml. Preferably, initial dose levels will be selected based on their ability to achieve ambient concentrations shown to be effective in in vitro models and in vivo models and in clinical trials, up to maximum tolerated levels. The dose of a particular drug and duration of therapy for a particular patient can be determined by the skilled clinician using standard pharmacological approaches in view of the above factors. The response to treatment may be monitored by analysis of blood or body fluid levels of the compound according to this invention, measurement of activity of the compound or its levels in relevant tissues or monitoring disease state in the patient. The skilled clinician will adjust the dose and duration of therapy based on the response to treatment revealed by these measurements.

Typically, the compositions described above will be combined or used together or in coordination with one or more other therapeutic substances, e.g., other drugs presently used in treating tuberculosis The compound of Formula I, or a synergistic combination of inhibitors, will of course be administered at a level (based on dose and duration of therapy) below the level that would kill the animal being treated. Preferably, administration will be at a level that will not irreversibly injure vital organs, or will not lead to a permanent reduction in liver function, kidney function, cardiopulmonary function, gastrointestinal function, genitourinary function, integumentary function, musculoskeletal function, or neurologic function. On the other hand, administration of inhibitors at a level that kills some cells which will subsequently be regenerated (e.g., endometrial cells) is not necessarily excluded.

EXAMPLES

In order to facilitate a more complete understanding of the invention, a number of Examples are provided below. However, the scope of the invention is not limited to specific embodiments disclosed in these Examples, which are for purposes of illustration only.

Example 1

Synthesis of Substitued Sulfonylamides

To illustrate the synthetic method shown in Scheme 1, a 25 g synthesis of III-50 was carried out.

Methyl n-Octylthioacetate. Octyl bromide (50.21 g., 0.26 mole), methyl thioglycoate (22.35 ml, 26.53 g, 0.25 mole) and potassium carbonate (34.5 g, 0.25 mole) were charged into a 1 L round-bottomed flask. To this mixture was added 350 ml of acetone and the suspension was refluxed for 48 h. After cooling to room temperature, the reaction mixture was filtered with the aid of acetone. The filtrate was evaporated under reduced pressure and the residue thus obtained was purified by distillation under reduced pressure. The fraction distilling at 118-121° C./3.8 mm Hg was collected. Yield: 48 g; 88%

IR (neat): 2924, 1736, 1435, 1278, 1133, 1011 cm$^1$. $^1$H NMR (CDCl$_3$): δ 3.64 (s, 3H), 3.13 (s, 2H), 2.52 (t, 2H, J=7.2 Hz), 1.47 (m, 2H), 1.2-1.4 (m, 10H), 0.88 (t, 3H, J=6.8 Hz). $^{13}$C, NMR: (CDCl$_3$): δ 13.9, 22.5, 28.6, 29.0, 29.02, 31.6, 32.5, 33.3, 52.1, 171.0.

Methyl n-Octanesulphonylacetate. A 3 L three-necked round-bottomed flask (fitted with a mechanical stirrer) was charged sequentially with ammonium heptamolybdate tetrahydrate (56 g, 0.045 mole), methyl n-octylthioacetate (40 g, 0.183 mole) and 1.5 L absolute alcohol (Schultz, H S, Freyermuth, H B., and Buc, S R., *J. Org. Chem.* 28:1140-1142, 1963). the vigorously stirred solution was cooled to 0° C. and to this cooled solution was added 104 ml of 30% hydrogen peroxide solution (0.732 mole) over a period of 1 h. The reaction mixture was allowed to warm to room temperature over a period of 2 h and then stirred for another 24 h when thin layer chromatography on silica showed complete disappearance of the starting material. The reaction mixture was filtered and the filtrate was evaporated under reduced pressure. The residue thus obtained was dissolved in ethyl acetate (1 L) and washed with water (100 ml×2), brine (100 ml). The organic layer was dried over anhydrous MgSO$_4$ and, after filtration of the solvents, was evaporated under reduced pressure to obtain the sulfone as a waxy solid, 36 g, 78%. The produce appeared to be pure (>95%) by NMR and was submitted to the next reaction without further purification.

IR (neat): 2919, 2848, 1743, 1460, 1437, 1329, 1278, 1218, 1137, 1108, 1010, 912, 723 cm$^{-1}$. $^1$H NMR (CDCl$_3$): δ 3.96 (s, 2H), 3.79 (s, 3H), 3.21 (t, 3H, J=8 Hz), 1.80 (m, 2H), 1.20-1.45 (m, 10H), 0.81 (t, 3H, J=6.7 Hz). $^{13}$C NMR (CDCl$_3$): δ 13.9, 21.7, 22.4, 28.2, 28.7, 28.8, 31.5, 53.1, 53.4, 57.0, 163.4.

n-Octanesulphonylacetamide. A solution of methyl n-octanesulphonylacetate (35 g, 0.143 mole) in 350 ml of anhydrous methanol was stirred magnetically at room temperature. To this solution was added 24 ml of aqueous ammonium hydroxide (27%, 6.48 g, 0.185 mole) in drops over a period of 30 minutes. The solution was stirred for 24 h and the white precipitate formed was filtered. The solid was recrystallized from hot ethyl acetate to obtain the required acetamide III-50 as a crystalline solid, mp. 140-142° C., 33 g, 97.6%.

IR (neat): 3386, 2920, 1659, 1420, 1315, 1286, 1129, cm$^{-1}$. $^1$H NMR (CDCl$_3$): δ 6.56 (br s, 1H, NH), 5.69 (br s, 1H, NH) 3.86 (s, 2H), 3.14 (app 1:1:1 triplet, J app=8.0 Hz, 2H), 2.16 (m, 2H), 1.86 (m, 2H), 1.1-1.3 (m, 12H), 0.86 (t, J=7.1 Hz, 3H). $^{13}$C NMR (CD$_3$COCD$_3$): δ 14.7, 22.9, 23.6, 29.4, 30.1, 30.15, 30.8, 32.8, 54.0, 164.8 HRMS calculated for C$_{10}$H$_{25}$N$_2$O$_3$S (M+NH$_4^-$) 253.1586, found 253.1587.

Example 2

Synthesis of Substituted Sulfonylamides

To illustrate the synthetic methods shown in Scheme 2 below, the following syntheses of compounds I-31 and I-89 were carried out.

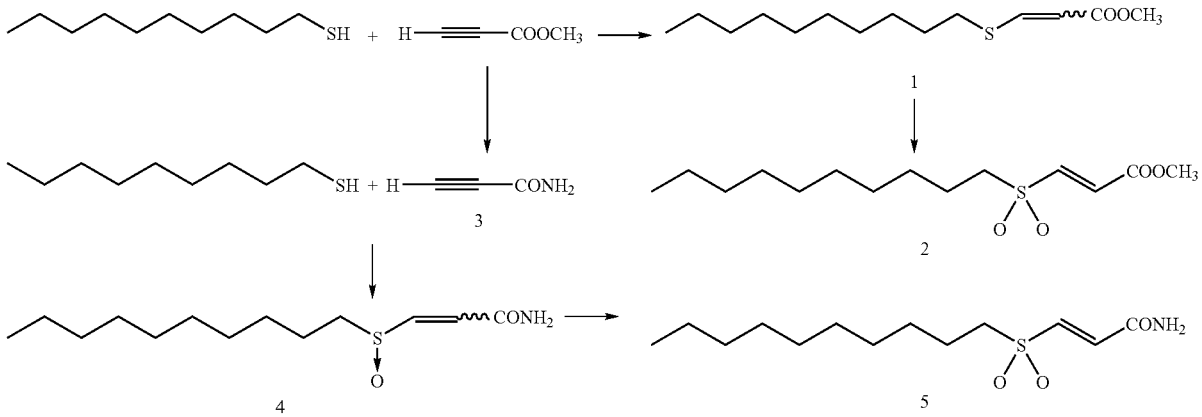

Scheme 2

(E/Z)-3-decylsulfanyl-acrylic acid methyl ester (1): Triethylamine (0.5 mL, 3.6 mmol) was added dropwise to a solution of decanethiol (2.5 mL, 12.1 mmol) and methyl propiblate (4.3 mL, 48.3 mmol) in dichloromethane (20 mL). The solution was stirred at room temperature for 20 min, under argon, after which it was diluted with water (60 mL) and extracted with dichloromethane (3×60 mL). The organic layer was washed with water (2×60 mL), brine (60 mL), dried over anhydrous magnesium sulfate, and concentrated in vacuo. Purification by flash chromatography (silica gel, ethyl acetate:hexanes 1:49) yielded a clear oil (3.06 g, 98%) as a mixture of isomers (E:Z, 6:1), which was carried through to the next step.

E isomer: IR (neat, cm$^{-1}$): 2920, 2848, 1712, 1580, 1460, 1430, 1300, 1255, 1215, 1160, 1041, 1015, 945, 827, 715, 697. $^1$H NMR (CDCl$_3$) δ 0.88 (t, 3H, J=6.7 Hz), 1.26 (bs, 12H), 1.40 (m, 2H), 1.67 (quint, 2H, J=7.3 Hz), 2.78 (t, 2H, J=7.4 Hz), 3.72 (s, 3H), 5.74 (d, 1H, J=15.2 Hz), 7.70 (d, 1H, J=15.2 Hz). Z isomer: IR (neat, cm$^{-1}$): 2920, 2848, 1712, 1580, 1460, 1430, 1300, 1255, 1215, 1160, 1041, 1015, 945, 827, 715, 697. $^1$H NMR (CDCl$_3$) δ 0.88 (t, 3H, J=6.7 Hz), 0.9-1.9 (app. s & several m, 16H), 2.77 (t, 2H, J=7.4 Hz), 3.75 (s, 3H), 5.85 (d, 1H, J=10.2 Hz), 7.1 (d, 1H, J=10.2 Hz).

(E)-3-decylsulfanyl-acrylic acid methyl ester (2): Compound 1 (0.50 g, 1.93 mmol), was dissolved in methanol (8.0 mL), and cooled to 0° C., added to a solution of oxone (1.84 g, 6.0 mmol) in water (8.0 mL, 49.5%) at 0° C., and stirred for 4 h at room temperature. The reaction was then diluted with water (60 mL), and extracted with chloroform (3×60 mL). The organic extract was washed with water (2×60 mL), brine (60 mL), dried over anhydrous magnesium sulfate, and concentrated in vacuo. Purification by flash chromatography (silica gel, ethyl acetate:hexanes 1:1) yielded white crystals (0.53 g, 93%) as a mixture of isomers (E:Z, 6:1). Purification by preparative TLC (ethyl acetate:hexanes 1:1) yielded compound 2 as white crystals.

mp 62-63° C.; IR (CH$_2$Cl$_2$, cm$^{-1}$): 3060, 2950, 2920, 2845, 1730, 1470, 1435, 1280, 1230, 1165, 1130, 995, 965, 815, 765, 690, 573. $^1$H NMR (CDCl$_3$) δ 0.88 (t, 3H, J=6.7 Hz), 1.27 (bs, 12H), 1.43 (m, 2H), 1.80 (sym. m, 2H), 3.05 (sym. m, 2H), 3.86 (s, 3H), 6.88 (d, 1H, J=15.3 Hz), 7.34 (d, 1H, J=15.3 Hz). Calculated for C$_{14}$H$_{26}$O$_4$S: C, 57.90, H, 9.02, S, 11.04. Found: C, 57.94, H, 9.12, S, 11.16.

Propiolamide (3): Methyl propiolate (2.0 mL, 22.5 mmol) was added to liquid ammonia at −78° C. and stirred for 2 hours. Evaporation at room temperature yielded compound 3 as white crystals (1.46 g, 94%).

mp 58-61° C. (lit.[5], 61-62° C.); $^1$H NMR (D$_2$O) δ 3.50 (s, 1H), 4.43 (bs, 2H).

(E/Z)3-decylsulfanyl-propionamide (4): Triethylamine (0.5 mL, 3.6 mmol) was added dropwise to a solution of decanethiol (1.36 mL, 6.56 nmol) and propiolamide (1.80 g, 26.1 mmol) in dichloromethane (20 mL). The solution was stirred at room temperature for 20 min under argon, after which it was diluted with water (60 mL) and extracted with dichloromethane (3×60 mL). The organic layer was washed with water (2×60 mL), brine (60 mL), dried over anhydrous magnesium sulfate, and concentrated in vacuo. Purification by flash chromatography (silica gel, ethyl acetate:hexanes 3:1),yielded compound 4 as white crystals (1.45 g, 91%) as a mixture of isomers (E:Z, 1:10), which was carried through to the next step.

Mixture of isomers: mp 65-70° C.,; IR (CH$_2$Cl$_2$, cm$^{-1}$): 3400, 3330, 3280, 3200, 2920, 2840, 1725, 1650, 1570, 1460, 1400, 1300, 1190, 770. E-isomer: $^1$H NMR(CDCl$_3$) δ 0.89 (t, 3H, J=6.8 Hz), 1.27 (bs, 12H), 1.41 (m, 2H), 1.70 (m, 2H), 2.74 (t, 2H, J=7.5 Hz), 5.4 (bs, 2H, NH$_2$), 5.82 (d, 1H, J=10.1 Hz), 6.95 (d, 1H, J=10.1 Hz).

(E)-3-decylsulfonyl-propionamide (5): Compound 4 (0.50 g, 2.05 mmol) was dissolved in methanol (8.0 mL), cooled to 0° C. and added to a solution of oxone (1.84 g, 6.0 mmol) in water. (8.0 mL, 49.5%) at 0° C. and stirred for 4 h at room temperature. The solution was then diluted with water (60 mL), and extracted with chloroform (3×60 mL). The organic extract was washed with water (2×60 mL), brine (60 mL), dried over magnesium sulfate, and concentrated in vacuo. Purification by flash chromatography (silica gel, ethyl acetate:hexanes 17:3) yielded compound 5 as white crystals (0.52 g, 92%) as a mixture of isomers (E:Z, 6:1). Purification by preparative TLC (ethyl acetate:hexanes 3:1) yielded compound 5 as white crystals.

mp 148-149° C.; IR (CHCl$_3$, cm$^{-1}$): 3390, 3140, 3060, 2920, 2840, 1700, 1615, 1455, 1395, 1320, 1130, 960, 814. $^1$H NMR (CDCl$_3$) δ 0.089 (t, 3H, J=6.8 Hz), 1.27 (bs, 12H), 1.43 (m, 2H), 1.80 (m, 2H) 3.05 (sym. m, 2H), 5.67 (bs, 1H, NH), 5.85 (bs, 1H, NH), 6.94 (d, 1H, J=14.8 Hz), 7.35 (d, 1H, J=14.8 Hz). Calculated for C$_{13}$H$_{25}$NO$_3$S: C, 56.70, H, 9.15, N 5.09, S 11.64. Found: C, 56.78, H, 9.16, N, 5.04, S, 11.76.

Example 3

In vitro Activity of Sulfones and Sulfoxides Against Mycobacteria

Various compounds were tested as described in U.S. Pat. No. 5,614,551 to determine minimum inhibitory concentratios (MIC) of the compounds against drug-resistant MTB (M. tuberculosis strain H37Rv), M. avium-intracellular, and M. bovis BCG. The results are shown in Table 1. Dose-response curves for the compound, designated III-50, have demonstrated an MIC of 6.5 μg/ml against the virulent strain of M. tuberculosis, H37Rv, and 6.25 μg/ml for M. bovis BCG. Dose-response curves for the compound designated S-I-73 have demonstrated an MIC of 3.12 μg/ml against MTB and 12.50 μ/ml against M. avium-intracellular. Tests using a compound according to Formula I having R=C$_8$H$_{17}$, Z=NH and Y=—CO—O—CH$_3$ against M. tuberculosis, H37Rv, demonstrated an MIC of 12.5 μg/ml.

Example 4

III-50 Inhibits Mycolic Acid Synthesis via a Target Different From Isoniazid

Figure 2:
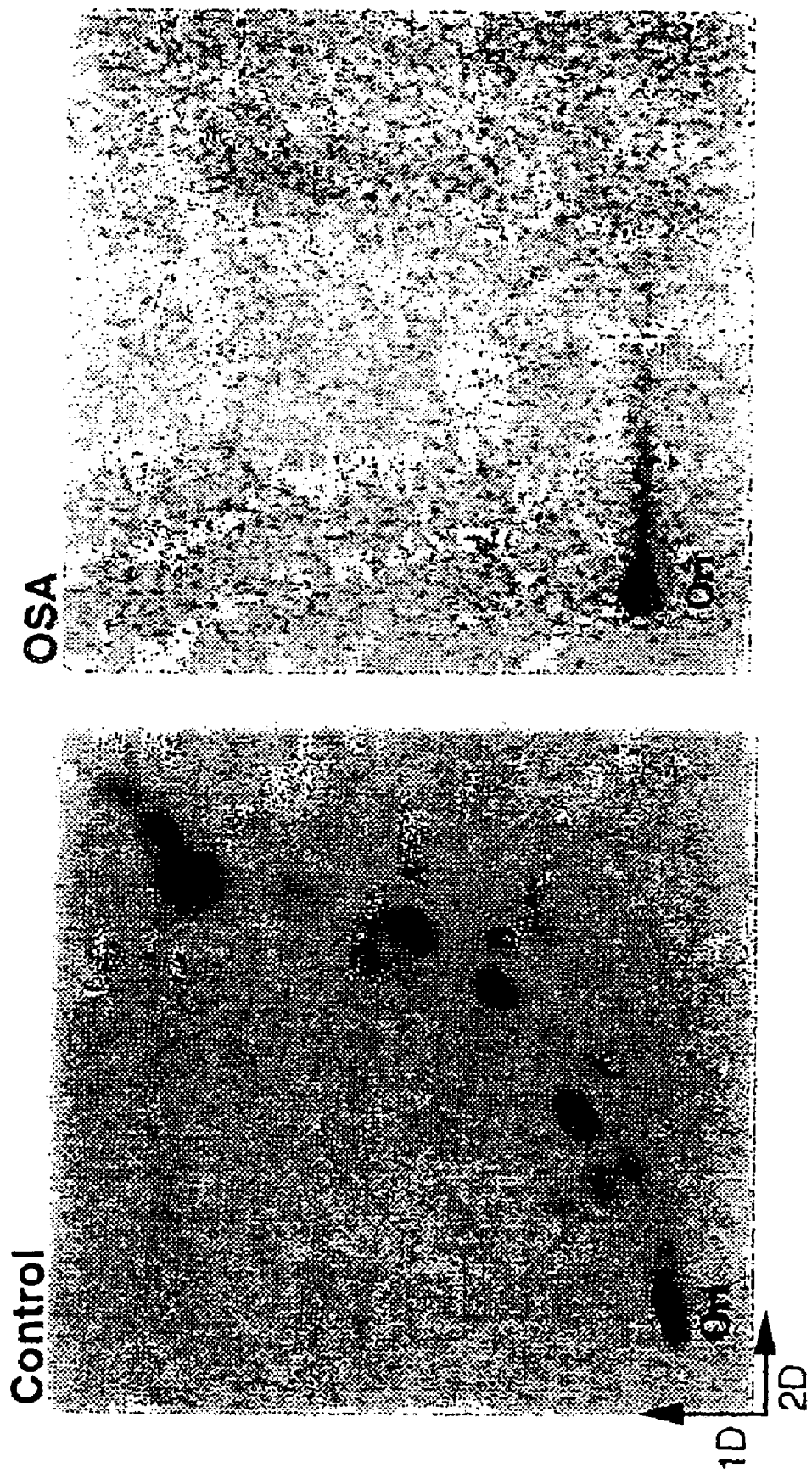
FIG. 2 shows two-dimensional thin layer chromatography of mycolic acids extracted from *M. avium-intracellulare* (Left Panel) and the same extract following treatment with n-octanesulphonylacetamide (Right Panel).

In a series of metabolic labeling experiments, the activity of a number of lipid metabolic pathways were studied in the presence and absence of III-50 using two-dimensional thin-layer chromatography and phosphorimage quantification. The TLC plates were spotted with mycobacterial acid methanolysates and developed in the first direction with petroleum ether (bp 60-80° C.):acetone (95:5, v/v, 3 times) and in the second direction with toluene:acetone (97:3), v/v, once). Abbreviations in FIG. 2 are: Ori=origin; A=α-mycolate; B=ketomycolate; and C=ω-mycolate. The left hand panel shows acid methanolysates from M. avium-intracellulare control cultures. The right hand panel shows acid methanolysates from M. avium-intracellulare cultures treated with 12.5 μg/ml n-octanesulphonylacetamide (III-50).

While minor qualitative and quantitative alterations of various lipid species were identified, the most profound effect was noted upon mycolic acid synthesis. Reproductions of the phosphorimages (FIG. 2) demonstrate that in the presence of III-50 mycolic acids are undetectable in M. avium-intracellulare and significantly reduced in M. bovis BCG. More importantly, while inhibition of mycolic acid synthesis is thought to be the mechanism of action of isoniazid (Takayama, et al., 1972 & 1975; Quemard, et al., 1993 & 1996; and Baldock, et al.), III-50 inhibits both the growth of *M. avium-intracellulare*, which is routinely isoniazid resistant (>2.5 µg/ml), and also an isoniazid (INH) resistant *M. tuberculosis* (>0.4 µg/ml). Thus, although both duced by electrophilic or free radical addition at the double bond between the acyl group and the sulfur atom.

Using the method of synthesis of vinyl sulfones 2 and 5, it is possible to prepare collections of screenable compounds by combinatorial methods. This is illustrated in Scheme 3.

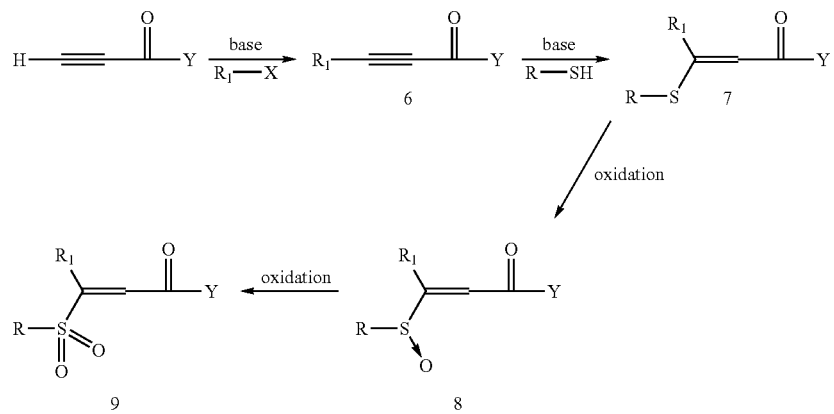

isoniazid and III-50 inhibit mycolic acid synthesis, the enzymatic target of III-50 within the mycolic acid synthetic pathway appears to differ from that of isoniazid.

Figure 3A:
FIGS. 3A and 3B show photomicrographs of *M. bovis* BGC with (B) or without (A) prior n-octanesulphonylacetamide treatment.
Figure 3B:
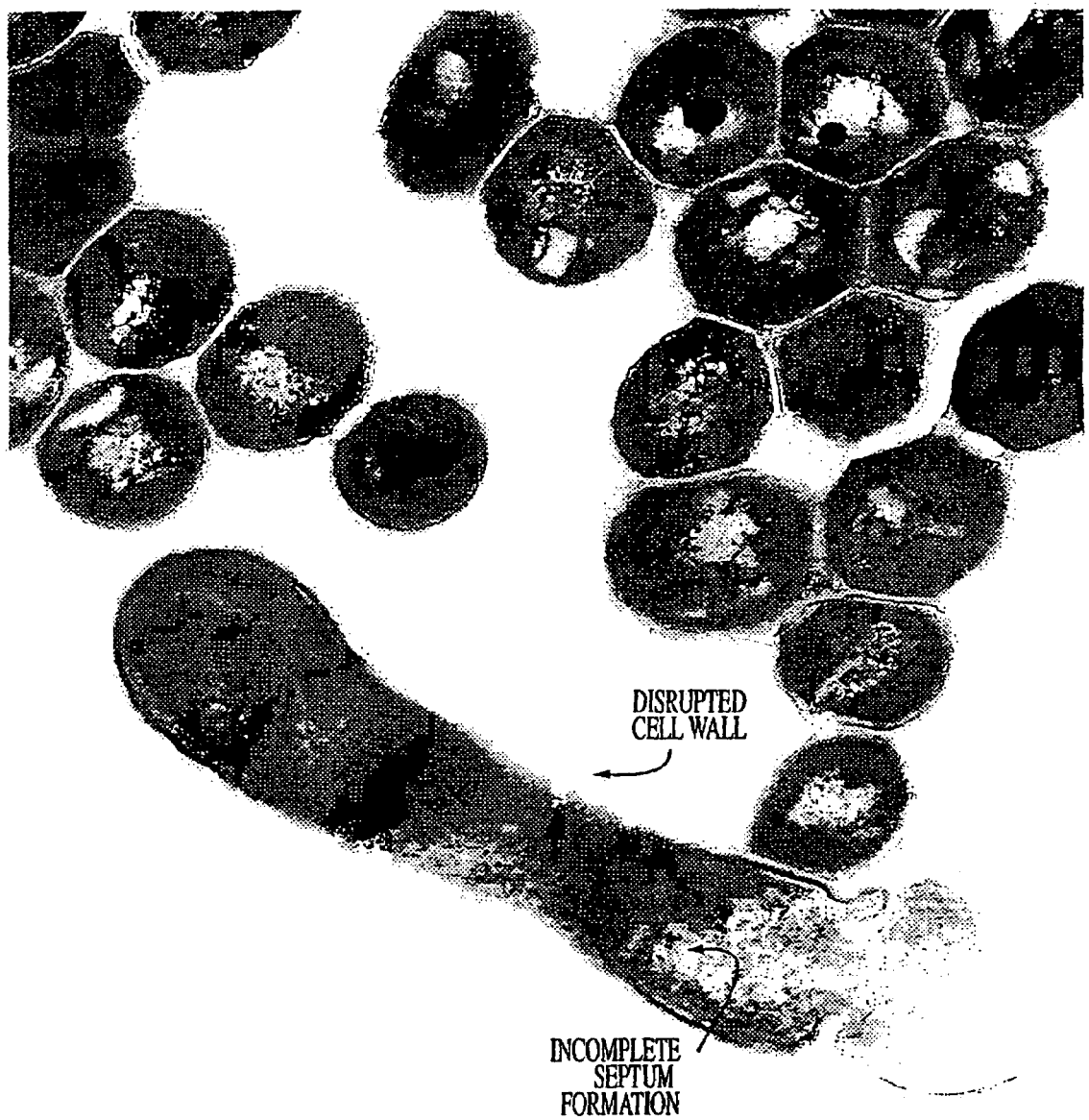

Inhibition of mycolic acid synthesis leads to the disruption of the cell wall in mycobacteria. FIG. 3 shows electron micrographs which depict cell division of *M. bovis* BCG in the presence (Panel A) and absence (Panel B) of III-50. Note, in the control, the well-developed cell wall and septum as the bacterium divides. In contrast, in the presence of III-50, there is disruption of the cell wall likely as a result of inhibition of mycolic acid synthesis.

Preparation of a Combinatorial Library of Sulfonamide Compounds

This invention contemplates combinatorial libraries that contains compounds of Formula II:

R—SO$_n$—CH=CH—CO—Y  Formula II where the various symbols have the same meaning as in Formula I, except that one or both of the vinyl hydrogens may be independently replaced by a group selected from alkyl, acyl, aryl, aralkyl, halogen; substituted or unsubstituted thiol; unsubstituted or substituted amino; hydroxy, and OR' wherein R' is selected from the group consisting of hydrogen, alkyl, acyl, aryl aralkyl, unsubstituted or substituted amino; substituted or unsubstituted thiol; and halogen; and a linear or cyclic carbon chain optionally interrupted with one or more heteroatom, and optionally substituted with one or more =O, or =S depending on the choice of electrophile in Scheme 3, or both vinyl hydrogens are replaced by a linear carbon chain to form a cyclic carbon moiety optionally interrupted with one or more heteroatoms, and optionally substituted with one or more =O, or =S. Typically, the groups substituted at the vinyl positions will have from 1 to 20 carbons in aggregate, and the heteroatoms will generally be selected from B, N, O, P, and S, more usually N, O, and S. The combinatorial library of this invention may also include derivatives of Formula II pro- The acidity of the acetylenic hydrogen in methyl propiolate or propiamide 3 allows its ready removal by base and reaction with electrophiles R$_1$—X (halides, aldehydes, ketones, esters, etc.) to give 6. Thiols R—SH can be added to 6 in the presence of mild base (i.e., potassium or sodium carbonate, triethylamine, etc.) to give trans- or trans/cis-mixtures of variously substituted sulfanylacylic esters or amides. Oxidation selectively to sulfoxides 8 or sulfones 9 can be carried out. Cis- and trans-isomers can be separated by crystallization or chromatographically. By varying R$_1$—X and R—SH or the identity of the ester or amide, a combinatorial library can be prepared.

The use of combinatorial libraries of diverse chemical compounds in drug discovery is well known (Moos, et al. (1993), Ann. Rep. Med. Chem., vol. 28, chap. 33, pp. 315-324, Academic Press; Gordon, etal. (1994), J. Med. Chem., 37:1385-1401). Methods of screening such libraries are described, e.g., in Gordon, et al., and references cited therein. Combinatorial libraries comprising compounds according to this invention, including vinyl sulfones or sulfoxides prepared as described in Scheme 3, may be screened for biological activity by any suitable screening procedure.

In an exemplary screening procedure, members of a library could be tested for ability to inhibit growth of *Toxoplasma gondii* using a test system described in U.S. Pat. No. 5,614,551, incorporated herein by reference. For example, toxicity, fibroblast lysis and growth of *T. gondii* can be monitored in 24 well tissue culture plates containing human foreskin fibroblasts. Seven serial dilutions of three members of the library can be compared to three control wells in each 24 well plate. Using multiple plates, large numbers of compounds from the library can be screened for their effect on *T. gondii*. Alternatively, using fewer dilutions, more compounds may be tested in each plate. Similar screening may be performed using *Mycobacterium* sp. in test systems described in U.S. Pat. No. 5,614,551 to identify compounds in a combinatorial library which affect mycobacteria. Other test systems suitable for screening compounds in combinatorial libraries according to this invention for their effects on other pathogens and/or neoplastic cells are readily available to the skilled worker, in view of the teachings herein.

Alternatively, the library may be screened for inhibitory effect on an enzyme such as fatty acid synthase (FAS). Suitable assay procedures are described in U.S. Pat. No. 5,759,837, incorporated herein by reference, and multi-well plates may be used to perform simultaneous FAS assays in the presence and absence of numerous members of the library to compare the inhibitory effect of various member compounds. In another alternative, binding affinity of member compounds for a particular receptor may be compared. Using a suitable assay that measures progress of a biological process, the skilled worker can readily design a suitable screening procedure to screen the combinatorial library of this invention for biological effect.

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, immunology, infectious diseases, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication, patent, or patent application was specifically and individually indicated to be incorporated by reference.

TABLE 1

In Vitro Activities of Sulfones and Sulfoxides against *M. tuberculosis*

| Compound # | Structure | MIC (ug/ml) MTB | BCG | MAI |
|---|---|---|---|---|
| SI-73 | | 3.12 | | 12.50 |
| HIII-50 | | 6.25 | 6.25 | 25.00 |
| SI-46 | | 6.25 | | |
| SI-52 | | 6.25 | | |
| HIII-206a | | 6.25 | | |
| HIII-206b | | 12.50 | | |
| SI-45 | | 12.50 | | 25.00 |
| HIII-302 | | >25 | | |

TABLE 1-continued

In Vitro Activities of Sulfones and Sulfoxides against *M. tuberculosis*

| Compound # | Structure | MIC (ug/ml) MTB | BCG | MAI |
|---|---|---|---|---|
| SI-48 | CH3(CH2)9-SO2-CH2-C(O)-NH-CH2-CH(OH)-CH2OH | >25 | | |
| HIII-56 | CH3(CH2)7-SO2-NH-CH2-COOH | >25 | >25 | |
| DI-59 | CH3(CH2)9-SO2-CH2-CH2-C(O)-NH2 | >25 | | |
| JRG-I-89-2 | CH3(CH2)10-SO2-CH=CH-CONH2 (trans) | 12.5 | | |
| JRG-I-89-1 | CH3(CH2)10-SO2-CH=CH-CONH2 (cis) | 25 | | |
| JRG-I-89-3 (mixture of cis and trans) | CH3(CH2)10-SO2-CH=CH-CONH2 | 6.25 | | |
| JRG-I-31 | CH3(CH2)10-SO2-CH=CH-COOMe | 12.5 | | |
| JRG-I-31 (mixture of cis and trans) | CH3(CH2)10-SO2-CH=CH-COOMe | 50 | | |
| JRG-I-43 | CH3(CH2)10-SO2-CH=CH-COOH | 50 | | |

MTB = *M. tuberculosis* (strain H37Rv)
BCG = *M. bovis*
MAI = *M. avium*-intracellulare
See legend in Appendix for Methods.

The invention claimed is:

1. A method of inhibiting growth of a mycobacterial cell, comprising administering an effective amount of a compound of formula I to the cell:

$$R-SO_n\text{-}Z\text{-}CO-Y \qquad \qquad I$$

wherein:
- R is selected from the group consisting of any alkyl group having from 6-10 carbon atoms, any unsaturated hydrocarbon having from 6-10 carbon atoms, or any alkyl group having from 6-10 carbon atoms interrupted by at least one aromatic ring;
- Z is —$CH_2$—;
- Y is selected from the group consisting of —$NH_2$, and —O—$CH_3$; and
- n is 1 or 2;

and wherein, the mycobacterial cell is selected from the group consisting of cells of *Mycobacteria tuberculosis*, drug resistant *M. tuberculosis, M. bovis, M. leprae*, and *M. paratuberculosis*.

2. The method of claim 1, wherein R is an alkyl group having 6-10 carbon atoms interrupted by an aromatic ring to give ortho-, meta-, or para-disubstitution.

3. The method of claim 1, wherein R is a branched alkyl group.

4. The method of claim 1, wherein R is an n-alkyl group.

5. The method of claim 1, wherein n is 1.

6. The method of claim 1, wherein n is 2.

7. The method of claim 1, wherein Y is —$NH_2$.

8. The method of claim 1, wherein: R is —$(CH_2)_9$—$CH_3$, n is 1, Z is —$CH_2$— and Y is —$NH_2$.

9. The method of claim 1, wherein: R is —$(CH_2)_7$—$CH_3$, n is 1, Z is —$CH_2$— and Y is —$NH_2$.

10. The method of claim 1, wherein: R is —$(CH_2)_9$—$CH_3$, n is 2, Z is —$CH_2$— and Y is —$NH_2$.

11. The method of claim 1, wherein: R is —$(CH_2)_7$—$CH_3$, n is 2, Z is $CH_2$— and Y is —$NH_2$—.

* * * * *